United States Patent
DiMauro et al.

(10) Patent No.: US 7,465,313 B2
(45) Date of Patent: Dec. 16, 2008

(54) RED LIGHT IMPLANT FOR TREATING DEGENERATIVE DISC DISEASE

(75) Inventors: Thomas DiMauro, Southboro, MA (US); Mohamed Attawia, Canton, MA (US); Jeffrey Sutton, Medway, MA (US)

(73) Assignee: Depuy Spine, Inc., Raynham, MA (US)

( * ) Notice: Subject to any disclaimer, the term of this patent is extended or adjusted under 35 U.S.C. 154(b) by 235 days.

(21) Appl. No.: 11/235,664

(22) Filed: Sep. 26, 2005

(65) Prior Publication Data

US 2007/0073363 A1 Mar. 29, 2007

(51) Int. Cl.
*A61N 5/06* (2006.01)
(52) U.S. Cl. .................... 607/92; 128/898; 607/88
(58) Field of Classification Search ............ 128/989; 607/88–94
See application file for complete search history.

(56) References Cited

U.S. PATENT DOCUMENTS

| | | | |
|---|---|---|---|
| 5,201,729 A * | 4/1993 | Hertzmann et al. | 606/2 |
| 5,259,380 A * | 11/1993 | Mendes et al. | 607/115 |
| 5,401,270 A * | 3/1995 | Muller et al. | 606/13 |
| 5,445,608 A * | 8/1995 | Chen et al. | 604/20 |
| 5,616,140 A | 4/1997 | Prescott | |
| 5,640,978 A | 6/1997 | Wong | |
| 5,800,478 A * | 9/1998 | Chen et al. | 607/88 |
| 5,948,008 A * | 9/1999 | Daikuzono | 607/89 |
| 6,063,108 A * | 5/2000 | Salansky et al. | 607/89 |
| 6,073,051 A | 6/2000 | Sharkey | |
| 6,409,719 B1 | 6/2002 | Manning | |
| 6,503,269 B2 | 1/2003 | Nield | |
| 6,537,304 B1 | 3/2003 | Oron | |
| 6,733,496 B2 * | 5/2004 | Sharkey et al. | 606/41 |
| 6,749,605 B2 * | 6/2004 | Ashley et al. | 606/41 |
| 2002/0045922 A1 * | 4/2002 | Nield et al. | 607/89 |
| 2002/0087206 A1 * | 7/2002 | Hirschberg et al. | 607/89 |
| 2002/0138073 A1 * | 9/2002 | Intintoli et al. | 606/15 |
| 2003/0125782 A1 * | 7/2003 | Streeter | 607/88 |
| 2006/0206172 A1 * | 9/2006 | DiMauro et al. | 607/88 |
| 2006/0271131 A1 * | 11/2006 | Passy et al. | 607/88 |
| 2006/0287695 A1 * | 12/2006 | DiMauro et al. | 607/88 |
| 2007/0073300 A1 * | 3/2007 | Attawia et al. | 606/73 |

FOREIGN PATENT DOCUMENTS

EP 1021223 10/2004

OTHER PUBLICATIONS

Akai, Laser's effect on bone and cartilage chance induced by joint immobilization: an experiment with animal model, Laser Surg Med., 1997, pp. 480-484, vol. 21(5).
Bjordal. A systematic review of low level laser therapy with location-specific doses for pain from chronic joint disorders, Australian Journal of Physiotherapy, 2003, pp. 107-116. vol. 49.
Bayat, Effect of low-power helium-neon laser irradiation on 13-week immobilized articular cartilage of rabbits, Indian J Exp Biol., 2004, pp. 866-860, vol. 42(9).
Bossy, In vitro survey of low energy laser beam penetration in compact bone, Acupunct Electrother Res., 1985, pp. 35-39. vol. 10(1-2).

(Continued)

*Primary Examiner*—Henry M Johnson, III

(57) ABSTRACT

Red light-emitting implants for treating degenerative disc disease.

3 Claims, 3 Drawing Sheets

OTHER PUBLICATIONS

Del Carlo, Nitric oxide-mediated chondracyte cell death requires the generation of additional reactive oxygen species, Arthritis Rheum., 2002, pp. 394-403, vol. 48(2).

Ebert, effect of irradiation with a low-intensity diode laser on the metabolism of equine articular cartilage in vitro, Am J Vet Res., 1998, pp. 1613-1618, vol. 59(12).

Guzzardella, Low-power diode laser stimulation of surgical osteochondral defects: results after 24 weeks, Artif Cells Blood Substit immobil Biotechnol., 2001, pp. 235-244, vol. 29(3).

Guzzardella, Laser stimulation on bone defect healing: an in vitro study, Lasers Med Sci., 2002, pp. 216-220, vol. 17(3).

Guzzardella, Assessment of low-power laser biostimulation on chondral lesions: an "in vivo" experimental study, Artif Cells Blood Substit Immobil Biotechnol., 2000, pp. 441-449. vol. 28(5).

Guzzardella, Cartilage cell stimulation with low-power laser: experimental assessment, Acta Bio Medica, 1999, pp. 43-47, vol. 70(3-4).

Jouzeau, Nitric oxide (NO) and cartilage metabolism: NO effects are modulated by superoxide in response to IL-1, Biorheology, 2002, pp. 201-214, vol. 39(1-2).

Khanna, Augmentation of the expression of proangiogenic genes in cardiomyocytes with low dose laser irradiation in vitro, Cardiovasc Radial Med., 1999, pp. 266-269, vol. 1(3).

Kipshidze, Lower-power hellum: neon laser irradiation enhances production of vascular endothelial growth factor and promotes growth of endothelial cells in vitro, Lasers Surg Med, 2001, pp. 355-364, vol. 28(4).

Kolari, Poor penetration of infra-red and helium neon low poser laser light into the dermal tissue, Acupunct Elecrother Res., 1993, pp. 17-21, vol. 18(1).

Kolarova, Penetration of the laser light into the skin in vitro, Lasers Surg. Med., 1999, pp. 231-235, vol. 24(3).

Matsushuta, Hypoxia-induced nitric oxide protects chondrocytes from damage by hydrogen peroxide. Inflamm Res., 2004, pp. 344-350, vol. 53(8). Epub Aug. 2004.

Nerlich, 1997 Volvo Award winner in basic science studies. Immunohistologic markers for age-related changes of human lumbar intervertebral discs, 1997. pp. 2781-1795, vol. 22(24).

Notzli, Laser Doppler flowmetry for bone blood flow measurements: helium-neon laser light attenuation and depth of perfusion assessment, J Orthop Res., 1989, pp. 413-424, vol. 7(3).

Pullin, Effects of holmium: YAG laser energy on cartilate metabolism, healing and biochemical properties of lesional and perilesional tissue in a weight-bearing model, Arthroscopy, 1996, pp. 15-25, vol. 12(1).

Reed, An in vivo study of the effect of excimer laser irradiation on degenerate rabbit articular cartilage, Arthroscopy, 1994, pp. 78-84, vol. 10(1).

Schemitsch, Evaluation of a laser Doppler flowmetry implantable fiber system for determination of threshold thickness for flow detection in bone. Calcif tissue Int., 1994, pp. 216-222, vol. 55(3).

Wang, Measuring dynamics of caspase-3 activity in living cells using FRET technique during apoptosis induced by high fluence low-power laser irradiation, Lasers Surg Med., 2005, pp. 2-7, vol. 36(1).

Ariga, Mechanical stress-induced apoptosis of endplate chondrocytes in organ-cultured mouse intervertebral discs, Spine, 2003, pp. 1528-1533, vol. 28(14), Lippincott William & Wilkins, Inc.

Borenstein, Epidemiology, etiology, diagnostic evaluation and treatment of low back pain, Curr Opin Rheumatol, 1999, pp. 15-17, vol. 11(2).

Carnevalli, Laser light prevents apoptosis in Cho K-1 cell line, J Clin Laser Med Surg, 2003, pp. 193-6, vol. 21(4), Mary Ann Liebert, Inc.

Cho, Effect of low-level laser therapy on Osteoarthropathy in Rabbit, In Vivo, 2004, pp. 585-592, vol. 18.

Herman, In vitro effects of Nd:YAG Laser radiation on cartilage metabolism, J Rheumatol, 1988, pp. 1818-26, vol. 15(12).

Iwatsuki, The effect of laser irradiation for nucleus pulposus: an experimental study, Neruol Res, 2005, pp. 319-23, vol. 27(3), W. S Maney & Son.

Jia, Effect of low-power he-ne laser irradiation on rabbit articular chondrocytes in vitro, Lasers in Surgery and Medicine, 2004, pp. 323-328, vol. 34, Wiley-Liss, Inc.

Lin, Effects of helium-neon laser on levels of stress protein and arthritic hist, Am J. Phys Med Rehabil, 2004, pp. 758-65, vol. 83(10), Lippincott, Williams & Wilkins.

Morrone, Biostimulation of human chondrocytes with Ga-Al-As diode laser: 'in vitro', Artif Cells Blood Substit Immobil Biotecchnol, 2000, pp. 193-201, vol. 28(2).

Rannou, Intervertebral Disc Degeneration, American Journal of Pathology, 2004, pp. 915-924, vol. 164(3), American Society for Investigative Pathology.

Schultz, Effects of Varying intensities of laser energy on articular cartilage: a pr, Laser Surg Med, 1958, pp. 577-88, vol. 5(6).

Shefer, Low-energy laser irradiation promotes the survival and cell cycle entry of skeletal muscle satellite cells, Journal of Cell Science, 2002, pp. 1461-9, vol. 115, The Company of Biologists Ltd.

Spivak, The effect of low-level Nd:YAG laser energy on adult articular in vitro, Arthroscopy: The Journal of Arthroscopc and Related Surgery, 1992, pp. 36-43, vol. 8(1), Raven Press Ltd.

Torricelli, Laser biostimulation of cartilage: in vitro evaluation, Biomed Pharmacother, 2001, pp. 117-20, vol. 55.

Wong-Riley, Light-emitting diode treatment reverses the effect of TTX on cytochrome oxidase in neurons, Neuroreport, 2001, pp. 3033-7, vol. 12(14).

Wong-Riley, Photobiomodulation directly benefits primary neurons functionally inactivated by toxins, J Biol Chem, 2005, pp. 4761-71, vol. 280(6).

* cited by examiner

RED LIGHT IMPLANT FOR TREATING DEGENERATIVE DISC DISEASE

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases ("MMPs"). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells to emit larger than normal amounts of the above-mentioned cytokines. In other instances of DDD, genetic factors, such as programmed cell death, or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins.

As DDD progresses, the toxic levels of the cytokines present in the nucleus pulposus begin to degrade the extracellular matrix. In particular, the MMPs (under mediation by the cytokines) begin cleaving the water-retaining portions of the proteoglycans, thereby reducing their water-retaining capabilities. This degradation leads to a less flexible nucleus pulposus, and so changes the load pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

Iwatsuki, Neurol. Res. 27, April 2005, 319-323 discloses laser irradiation of a nucleus pulposus with a 1,1014 nm Nd-YAG laser in an amount of 20 J/disc. Iwatsuki concludes that alteration of proteins and chemical factors such as prostaglandin E2 and phospholipase A2 within the disc are caused by heat produced by the laser irradiation.

SUMMARY OF THE INVENTION

The present inventors have noted that the literature reports that low level laser therapy may be effective in cartilage repair. As the intervertebral disc consists essentially of cartilage, the present inventors believe that red light irradiation of the intervertebral disc with light having a wavelength of between 600 nm and 1000 nm may provide a useful therapy to DDD. It is believed that red light having a wavelength of between 600 nm and 1000 nm initiates a photochemical reaction (independent of heat) that provides therapy to the disc.

The literature has consistently reported that red light irradiation of cartilage stimulates extracellular matrix production. For example, Spivak, Arthroscopy, 1992, 8(1) 36-43 applied 51-127 $J/cm^2$ of red light to full-thickness articular cartilage explants maintained in organ culture, and found stimulation of extracellular matrix synthesis at 6-7 days following laser exposure. Herman, J. Rheumatol. 1988, Dec. 15(12), 1818-26 assessed the in vitro affect of red light laser on mature normal bovine articular cartilage metabolism, and found that normal pulsed mode delivery of defined energy levels could be shown to consistently upregulate cartilage proteoglycan, collagen, non-collagen protein and DNA synthesis. Herman concludes that red light irradiation applied directly at surgery or via arthroscopy may provide a potential means of effecting cartilage healing. Jia, Lasers Surg. Medicine, 34, 323-328, 2004 examined the 1-6 $J/cm^2$ red light irradiation of rabbit articular cartilage in vitro, and found that irradiation produced considerably higher cell proliferation activity, and that 4-5 $J/cm^2$ irradiation produced a positive effect on synthesis and secretion of extracellular matrix. Jia concluded that low power laser irradiation treatment is likely to achieve the repair of articular cartilage in the clinic. Cho, In Vivo, 18, 585-92 (2004) examined the effects of low power red light irradiation upon the osteoarthritic knees of rabbits, and reported that regeneration of articular cartilage was seen in gross observation of the 4-week treatment group. Cho concluded that low power red light irradiation was effective in treating chemically-induced osteoarthritis.

Because one of the hallmarks of DDD is the degeneration of the ECM (leading to decreased disc flexibility), it is believed that red light irradiation of the disc will help the disc regain its flexibility.

Chondrocyte apoptosis is believed to play a major role in DDD. Rannou, Am. J. Pathology, 164(3), March 2004, 915-924, and Ariga, Spine, 28(14), 1528-33 (2003). The present inventors have further noted that low level laser therapy has been found to be effective in enhancing cell viability and preventing apoptosis. Morrone, Artif. Cells Blood Substit. Immobil. Biotechnol. 2000, March, 28(2) 193-201 examined the effects of 780 nm red light on cartilage cells in vitro and reported that the data showed good results in terms of cell viability and levels of calcium and alkaline phosphate in the groups treated with laser biostimulation. Torricelli, Biomed. Phamacother., 2001, Mar. 55(2) 117-20 evaluated the effect of red light upon chondrocyte cultures derived from rabbit and human cartilage, and found a positive biostimulation effect on cell proliferation and an increase in cell viability. Torricelli concluded that these results provide a basis for a rational approach to the experimental and clinical use of red light. Lin, Am. J. Phys. Med. Rehabil. 2004, Oct. 83(10), 758-65 evaluated the effect of red light irradiation upon stress proteins in induced arthritis, found the irradiation enhanced stress protein production in arthritic chondrocytes, and concluded that low power laser has a therapeutic effect in preserving chondrocytes. Schultz, Lasers Surg. Med. 1985, 5(6), 577-88 irradiated partial thickness cartilage defects in guinea pigs with red light and found that the knees exposed to 25-75 J demonstrated a reparative process with chondral proliferation.

In addition, low level laser therapy has also been found to prevent apoptosis in other non-cartilage systems as well. See Shefer, J. Cell Science, 115, 1461-9(2002) (skeletal muscle satellite cells) and Carnevalli, J. Clin. Laser. Med. Surg. 2003, Aug. 21(4), 193-6 (Cho K-1 cell line). Wong-Riley, J. Biol. Chem. 2004, e-pub Nov. 22, reports that irradiating neurons with 670 nm red light significantly reduced neuronal cell death induced by 300 mM KCN from 83.6% to 43.5%.

The literature has further reported that oxidative stress plays a major role in the beginning stages of DDD. Borenstein, *Curr. Opin. Rheumatol.*, 1999, Mar. 11(2) 151-7. Cho, *In Vivo*, 18, 585-92 (2004) examined the effects of low power red light irradiation upon the osteoarthritic knees of rabbits, and reported that anti-oxidant superoxide dismutase (SOD) activity increased 40%. Therefore, it appears that red light may be useful in treating the oxidative stress component of DDD as well.

Without wishing to be tied to a theory, it is further believed that the red light irradiation of cells upregulates cytochrome c oxidase activity in those cells. Cytochrome c oxidase (also known as complex IV) is a major photoacceptor. According to Wong-Riley, *Neuroreport*, 12:3033-3037, 2001, in vivo, light close to and in the near-infrared range is primarily absorbed by only two compounds in the mammalian brain, cytochrome c oxidase and hemoglobin. Cytochrome c oxidase is an important energy-generating enzyme critical for the proper functioning of many cell lines. The level of energy metabolism in cells is closely coupled to their functional ability, and cytochrome c oxidase has proven to be a sensitive and reliable marker of cellular activity.

By increasing the energetic activity of cytochrome oxidase, the energy level associated with cellular metabolism may be beneficially increased. Indeed, the literature reports that red light reverses the inhibitory effects of toxins upon cytochrome oxidase activity, leading to increased energy metabolism in neurons functionally inactivated by toxins. Wong-Riley *Neuroreport* 12(14) 2001: 3033-3037 and Wong-Riley, *J. Biol. Chem.*, e-pub, Nov. 22, 2004.

Accordingly, the present inventors have developed inventions for treating DDD based upon low level laser therapy that take advantage of this therapy's ability to induce cartilage repair and prevent apoptosis.

Therefore, in accordance with the present invention, there is provided a method of treating DDD, comprising the step of:
a) irradiating the intervertebral disc with an amount effective red light having a wavelength of between 600 nm and 100 nm.

DETAILED DESCRIPTION OF THE INVENTION

In some preferred embodiments, the therapeutic red light is delivered across the vertebral endplates adjacent the disc into the disc, preferably into the nucleus pulposus. This mode of delivery allows the clinician to avoid harming the disc. Such delivery can be effected by implanting a red light LED into the adjacent vertebral body, or by implanting a red light conduit into the adjacent vertebral body.

In other preferred embodiments, the therapeutic red light is delivered across the outside surface of the annulus fibrosus of the disc and preferably into the nucleus pulposus. Such delivery can be effected by anchoring a red light LED onto an outside surface of an adjacent vertebral body, and intradiscally directing the red light emitted by the LED.

In other preferred embodiments, the therapeutic red light is delivered to the disc through an intradiscal implant having a red light source.

Figure 1:
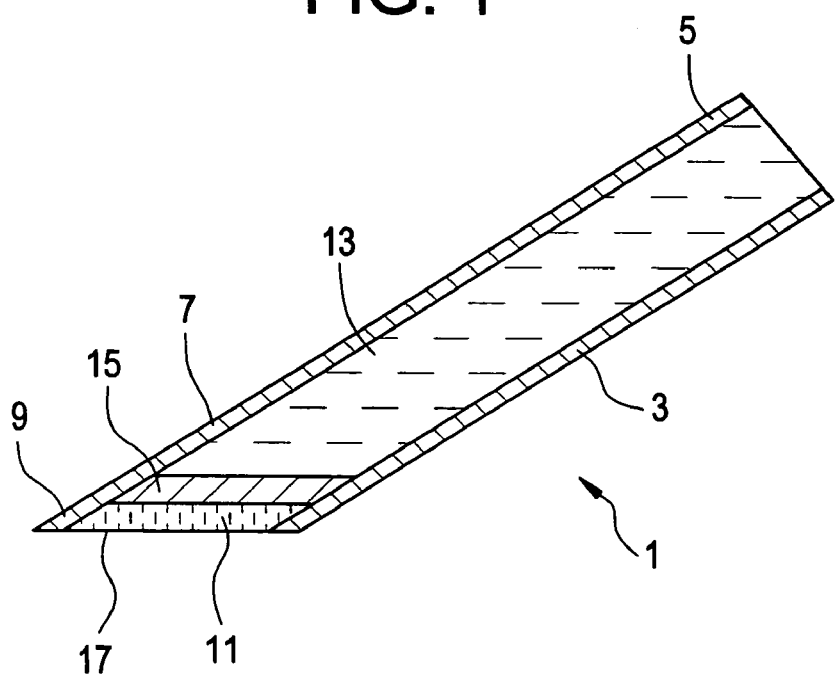
FIG. 1 is a cross-section of a preferred red light implant of the present invention.

Now referring to FIG. 1, there is provided an intraosteal red light implant 1 for treating DDD, comprising:
  a) a hollow tube 3 having a throughbore, a proximal end portion 5 and a distal end portion 7, the distal end portion forming a sharp tip 9.
  b) a red light translucent material 11 disposed within the throughbore at the distal end of the tube and forming an emission surface 17,
  c) a power source 13 disposed within the throughbore at the proximal end portion,
  d) a red light LED 15 disposed between the power source and translucent material.

Figure 2:
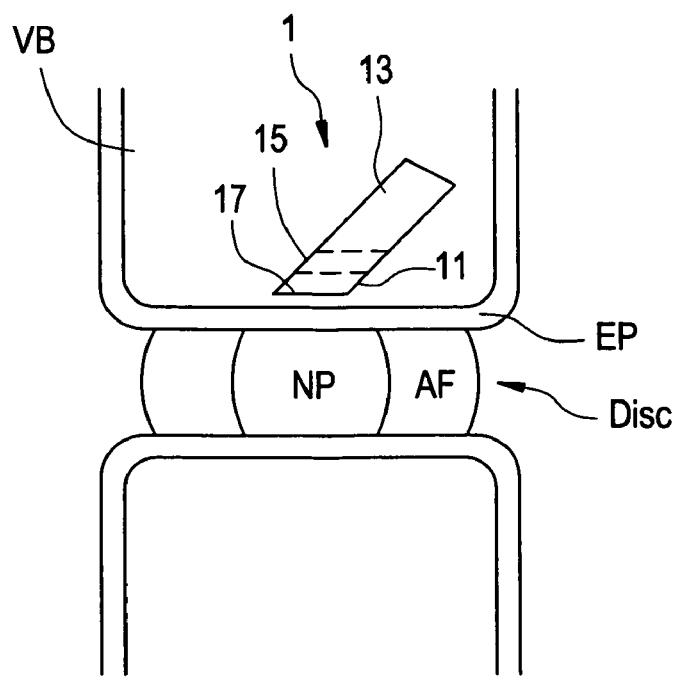
FIG. 2 is a cross-section of the implant of FIG. 1 embedded with a vertebral body.

Now referring to FIG. 2, in one preferred embodiments, there is provided a method of treating a degenerating disc comprising a nucleus pulposus NP and an annulus fibrosus AF, comprising the steps of:
a) implanting into a vertebral body VB an implant 1 comprising a red light source 15 and an emission surface 17,
b) orienting the implant 1 so that the emission surface 17 faces the vertebral endplate EP (preferably, the center of the vertebral endplate), and
c) powering the red light source 15 to transmit red light from the red light source 15 through the emission surface 17 and through the vertebral endplate EP to the intervertebral disc.

The implantation of the implant is preferably achieved by inserting the implant through the skin and soft tissue to contact the vertebral body slightly above and lateral to the pedicle, then puncturing the cortical rim of the vertebral body at that location with the sharp tip of the implant, then advancing the implant towards the center of the lower endplate of the punctured vertebral body. Once the implant arrives at the lower endplate, the implant is rotated to insure that the emission surface is essentially flush with the lower endplate, preferably the center of the lower endplate so that red light emitted from the implant crosses the endplate and irradiates the nucleus pulposus.

The hollow tube of the implant may be made out of any number of biocompatible materials, such as metal like titanium or CrCo, and ceramics such as alumina. If the implant includes an antenna as the power source, then it is preferred that the tube be a ceramic.

Preferably, the distal end portion of the tube is filled with a translucent material to form an emission surface. This translucent material (which is preferably substantially transparent to red light) acts as a conduit for red light emitted by the LED to be emitted from the distal end of the tube. The provision of this translucent material at the distal end also protects the red light LED from direct contact with body fluids. In some embodiments, the red light-translucent material comprises a red light translucent polymer. In other embodiments, the red light-transmissible implant comprises a UVB-translucent ceramic, such as glass. In preferred embodiments, the translucent material is silica. The glass content of the implant is preferably in the range of 20-40 volume percent ("v/o"). At higher glass contents, the implant becomes relatively inelastic. At lower fractions, red light transmission is more problematic. The red light translucent component of the implant may be in the form of beads, long fibers or chopped fibers.

Preferably, the distal end portion of the tube is shaped to form a sharp tip. This sharp tip provides two advantages. First, it can be used to penetrate the cortical rim of the vertebral body. Second, the angular nature of the tip produces an oval-shaped opening at the distal end (which is filled by the translucent material). The oval nature increases the surface area of the emission of the red light from the tube, thereby increasing the amount of tissue that can be therapeutically irradiated by the red light.

In the middle of the implant 1 lies the red light LED. Conventional red light LEDs that are commercially available may be used as the red light LED of the present invention.

In order to protect the active elements of the device from body fluids, in some embodiments, the red light LED is encased in a casing. This casing both protects the LED components from body fluids, and also prevents the LED components from eliciting a violent immune reaction In some embodiments, the casing is made of a red light transparent material. The red light transparent material may be placed adjacent the LED component so that red light may be easily transmitted therethrough. In some embodiments, the red light transparent casing is selected from the group consisting of silica, alumina and sapphire. In some embodiments, the light transmissible material is selected from the group consisting of a ceramic and a polymer. Suitable red light-transmissible ceramics include alumina, silica, CaF, titania and single crystal-sapphire. Suitable red light transmissible polymers are preferably selected from the group consisting of polypropylene and polyesters.

In the proximal portion of the implant lies the power source. In some embodiments, the power source can be a battery. The battery may be electrically coupled to a timer (not shown) that provides periodic energizing of the LED. In other embodiments, the power source can be an Rf antenna adapted to receive Rf energy for an external Rf antenna.

In some embodiments, energy (such as Rf energy or red light) is delivered transdermally and collected near the skin layer of the patient. Such a configuration would allow light to be delivered deep within the patient, or in or near critical organs or tissues, and yet have the light source and associated components in a less sensitive region. This configuration allows easier access to the light/controller should the need arise for service or maintenance, and also allows for more efficient transdermal energy transmission. Moreover, by using a hollow tube with reflective internal surfaces, light and therapeutic fluids could be delivered to the implanted device. The light source/controller implanted near the patient's skin could also be a simple, hollow chamber made to facilitate the percutaneous access described above. The advantages and benefits of this system include:

a) further removal from the deep site of the functional implant, thereby reducing risk of contamination of the deeper site by percutaneous access;
b) easier percutaneous access by being closer to the skin surface and having a larger surface area or target to access with the needle;
c) a larger volume could hold more therapeutic fluid to provide a longer duration of activity; and
d) a central reservoir could provide therapy to multiple implants throughout the body.

In use, the surgeon implants the implant into the spine of the patient so that the Rf receiving antenna is adjacent the posterior portion of the vertebral body.

Figure 3:
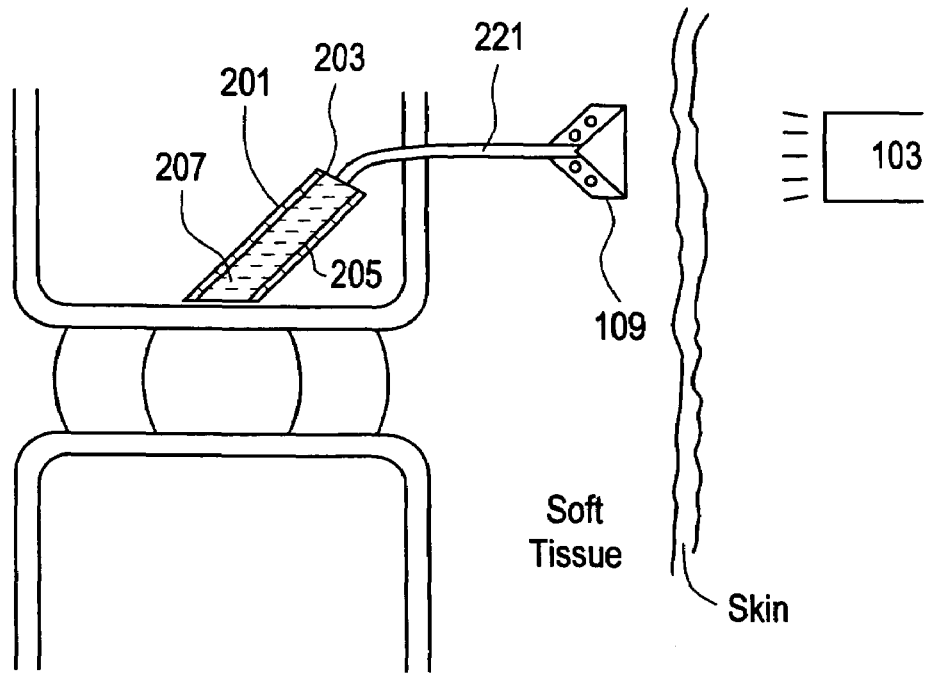
FIG. 3 is a cross-section of the implant of the present invention embedded with a vertebral body, wherein the implant has a subcutaneous red light collector.

In some embodiments wherein the red light is delivered transdermally, it may be advantageous to provide the red light collection closer to the skin. Now referring to FIG. 3, there is provided a first exemplary implant having an external light source. The externally based-control device has a light source for generating light within the device. The light generated by this source is transmitted through fiber optic cable 103 through the patient's skin to an internally-based light port 109. The light port is adapted to be in light-communication with a fiber optic cable 221 disposed upon the proximal surface 203 of the red light implant 201. The implant, which may be simply a metal tube 205 filled with silica 207, receives the light and transmits the light to the adjacent cancellous tissue.

Figure 4:
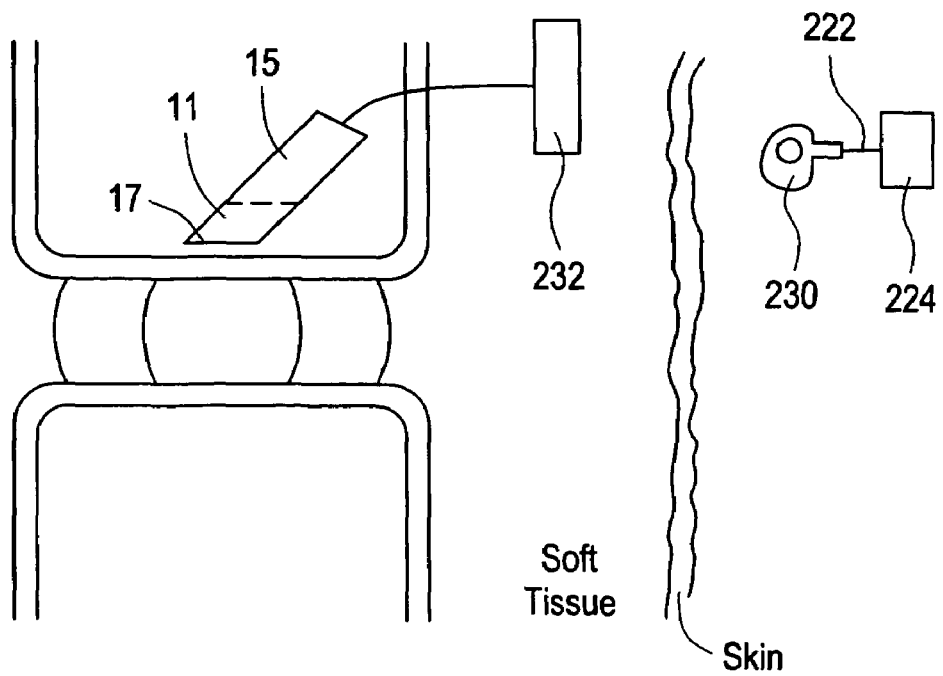
FIG. 4 is a cross-section of the implant of the present invention embedded within a vertebral body, wherein the implant has a subcutaneous Rf antenna.

Now referring to FIG. 4, there is provided a second exemplary red light unit having an internal light source. Externally based-control device 222 has an RF energy source 224 and an antenna 230 for transmitting signals to an internally-based antenna 232 provided on the prosthesis. These antennae 230, 232 may be electro-magnetically coupled to each other. The internal antenna 232 sends electrical power to a light emitting diode (LED) 15 disposed internally on the implant in response to the transmitted signal transmitted by the external antenna 230. The light generated by the LED travels across the red light transparent layer 11, across the endplate and into the disc.

In some embodiments, the implant having an internal light source further contains an internal power source, such as a battery (not shown). The battery, which could be re-chargeable, is controlled by an internal receiver and has sufficient energy stored therein to deliver electrical power to the light source in an amount sufficient to cause the desired light output.

When the implant is coupled with external energy, power can be transmitted into the internal device to re-charge the battery.

Figure 5:
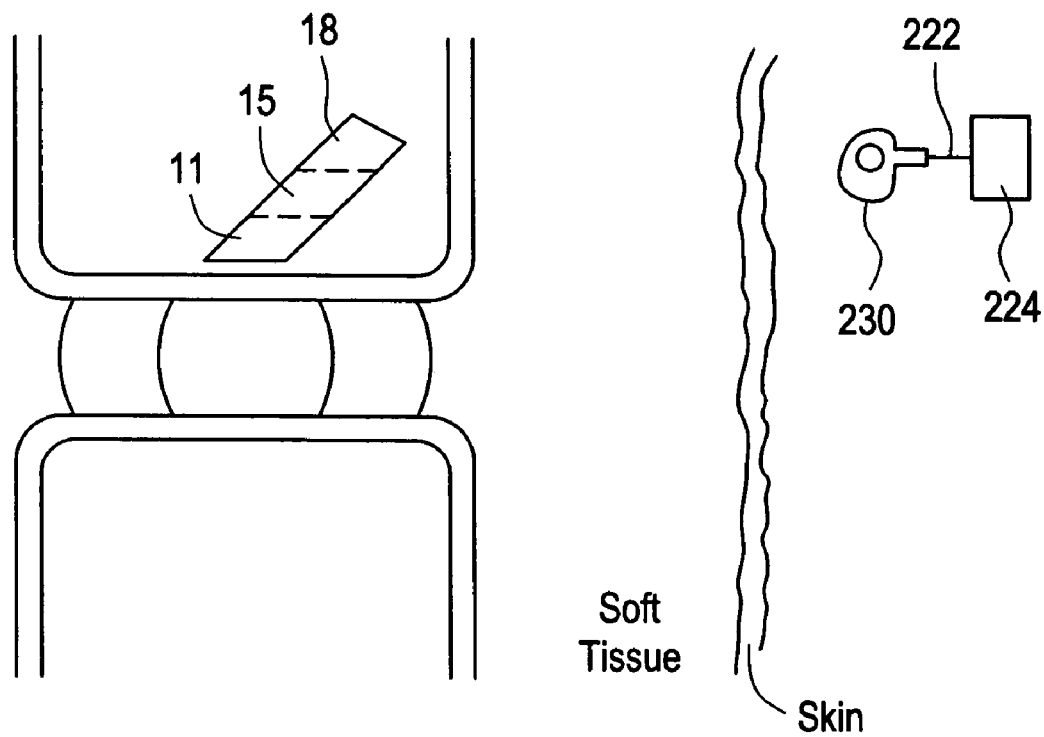
FIG. 5 is a cross-section of the implant of the present invention embedded with a vertebral body, wherein the implant has an Rf antenna contained within the vertebral body.

In some embodiments, the light generated by the implant is powered by wireless telemetry integrated onto or into the implant itself Now referring to FIG. 5, the LED 15 may comprise a radiofrequency-to-DC converter and modulator. When radiofrequency signals are emitted by the external antenna 230 and picked up by the internal antenna 18, these signals are then converted by the receiver (not shown) into electrical current to activate the light source of the red light unit.

In one embodiment, the implant may have an internal processor adapted to intermittently activate the LED.

In some embodiments, the telemetry portion of the device is provided by conventional, commercially-available components. For example, the externally-based power control device can be any conventional transmitter, preferably capable of transmitting at least about 40 milliwatts of energy to the internally-based antenna. Examples of such commercially available transmitters include those available from Microstrain, Inc. Burlington, Vt. Likewise, the internally-based power antenna can be any conventional antenna capable of producing at least about 40 milliwatts of energy in response to coupling with the externally-generated Rf signal. Examples of such commercially available antennae include those used in the Microstrain Strainlink™ device. Conventional transmitter-receiver telemetry is capable of transmitting up to about 500 milliwatts of energy to the internally-based antenna.

Figure 6:
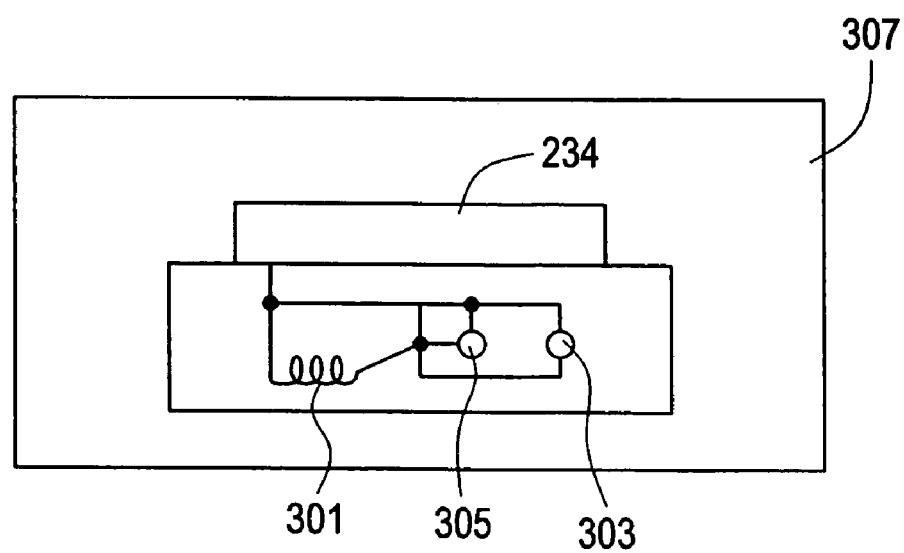
FIG. 6 is representative circuitry that may be included in the implants of the present invention.

In some embodiments, and now referring to FIG. 6, the implant includes a light emitting diode (LED) 234 built upon a portion 307 of the implant, along with the required components to achieve trans-dermal activation and powering of the device. These components can include, but are not limited to, RF coils 301, control circuitry 303, a battery 305, and a capacitor. Such a device could be capable of intermittent or sustained activation without penetrating the skin, thereby avoiding trauma to the patient and/or risk of infection from skin-borne bacteria. As shown above, the accessory items needed to power and control the LED may be embedded within the implant. However, they could also be located on the surface(s) of the implant, or at a site adjacent to or near the implant, and in communication with the implant.

To enhance the propagation of light emitted from the end of the device, a lens could be placed at the distal end of the device to spread the light, or a diffuser such as a small sheet or plate of optical material could be used to create more surface area. Alternatively, one could create a series of lateral diffusers, such as grooves or ridges, along the distal portion of end of the device to spread light out from 360 degrees perpendicular to the axis of the fiber, as well as emanating directly out from the end of the fiber.

The red light of the present invention has a wavelength of between about 600 nm and about 1000 nm. In some embodiments, the wavelength of light is between 800 and 900 nm, more preferably between 800 nm and 835 nm. In some embodiments, the wavelength of light is between 600 nm and 700 nm.

In some embodiments, the light source is situated to irradiate the intervertebral disc tissue with between about 0.02 $J/cm^2$ and 200 $J/cm^2$ energy. In some embodiments, the light source is situated to irradiate the intervertebral disc tissue with between about 0.2 $J/cm^2$ and 50 $J/cm^2$ energy, more preferably between about 1 $J/cm^2$ and 10 $J/cm^2$ energy. Because there is light-attenuating bony cortical tissue interposed between the red light implant and the target disc tissue, the energy exiting the emission surface of the implant is preferably somewhat higher than the energy values provided above.

In some embodiments, the light source emits lights consisting essentially of red light having a wavelength between 600 nm and 1000 nm. In others, the light source emits a wide spectrum of light and includes the emission of red light having a wavelength between 600 nm and 1000 nm with a strength of between about 0.02 $J/cm^2$ and 200 $J/cm^2$ energy. In one of these wide spectrum embodiments, white light is used as the light source. In some embodiments thereof, the device includes a filter that filters out at least some of the wavelengths outside of the 600-1000 nm range.

It is expected that the bony endplate will also serve to diffuse the red light so that it will irradiate a surface of the disc that is greater than the surface area of the emission surface.

In some embodiments, the light source is situated to produce an energy intensity of between 0.1 watts/$cm^2$ and 10 watts/$cm^2$. In some embodiments, the light source is situated to produce about 1 milliwatt/$cm^2$.

Therefore, in some embodiments of the present invention, the therapeutic dose of red light is provided on approximately a daily basis, preferably no more than 3 times a day, more preferably no more than twice a day, more preferably once a day.

In some embodiments, the implant of the present invention comprises an intervertebral motion disc and a red light source.

We claim:

1. A method of treating a degenerating disc comprising a nucleus pulposus and an annulus fibrosus, comprising the steps of:
    a) implanting into a vertebral body an implant comprising a red light source and an emission surface,
    b) powering the red light source to transmit red light from the red light source through the emission surface and the vertebral endplate to the intervertebral disc.

2. The method of claim 1 further comprising the step of:
    c) orienting the implant so that the emission surface faces the vertebral endplate.

3. The method of claim 2 wherein the emission surface faces a center of the vertebral endplate.

\* \* \* \* \*